United States Patent [19]

Immel et al.

[11] Patent Number: 5,338,885
[45] Date of Patent: Aug. 16, 1994

[54] PROCESS FOR THE PREPARATION OF DIPHENYLAMINES

[75] Inventors: Otto Immel; Gerhard Darsow; Hans-Josef Buysch, all of Krefeld, Fed. Rep. of Germany

[73] Assignee: Bayer Aktiengesellschaft, Leverkusen, Fed. Rep. of Germany

[21] Appl. No.: 950,613

[22] Filed: Sep. 24, 1992

[30] Foreign Application Priority Data

Oct. 4, 1991 [DE] Fed. Rep. of Germany ....... 4132945

[51] Int. Cl.$^5$ .............................................. C07C 209/26
[52] U.S. Cl. ................................................. 564/398
[58] Field of Search ................ 564/396, 422, 397, 398

[56] References Cited

U.S. PATENT DOCUMENTS

| | | | |
|---|---|---|---|
| 3,219,704 | 11/1965 | Wilder et al. | 260/576 |
| 4,057,581 | 11/1977 | Krall et al. | 260/571 |
| 4,729,977 | 3/1988 | Immel et al. | 564/402 |
| 4,804,783 | 2/1989 | Nagata et al. | 564/402 |
| 4,871,875 | 10/1989 | Nagata et al. | 564/402 |
| 4,902,661 | 2/1990 | Immel et al. | 502/184 |
| 4,952,731 | 8/1990 | Nagata et al. | 564/402 |

FOREIGN PATENT DOCUMENTS

| | | |
|---|---|---|
| 0208933 | 1/1987 | European Pat. Off. . |
| 0325132 | 7/1989 | European Pat. Off. . |
| 2331878 | 6/1973 | Fed. Rep. of Germany . |
| 2520893 | 5/1975 | Fed. Rep. of Germany . |
| 3801754 | 1/1988 | Fed. Rep. of Germany . |
| 2561238 | 9/1985 | France . |
| 1382206 | 6/1972 | United Kingdom . |

*Primary Examiner*—Richard L. Raymond
*Assistant Examiner*—Brian M. Burn
*Attorney, Agent, or Firm*—Sprung Horn Kramer & Woods

[57] ABSTRACT

Substituted or unsubstituted diphenylamnines can be obtained by reaction of substituted or unsubstituted anilines with substituted or unsubstituted cyclohexanones over a supported catalyst containing rhodium or a combination of rhodium with another platinum metal at 200°–450° C. and 0.1–20 bar.

11 Claims, No Drawings

PROCESS FOR THE PREPARATION OF DIPHENYLAMINES

BACKGROUND OF THE INVENTION

The invention relates to a process for the preparation of substituted or unsubstituted diphenylamines by reaction of the cyclohexanones and anilines on which they are based in the presence of a rhodium-containing supported catalyst.

For the preparation of diphenylamine and derivatives thereof, German Offenlegungsschrift 2,331,878 has disclosed a process in which the starting materials are imines, such as N-cyclohexylidene-aniline and derivatives thereof, which are dehydrogenated in the gas phase in the presence of supported catalysts based on nickel, platinum, palladium or copper/chromium.

Furthermore, German Offenlegungsschrift 2,520,893 has disclosed the preparation of diphenylamine by catalytic dehydrogenation of compounds and/or mixtures of compounds composed entirely or in part of hydrogenated diphenylamine in the presence of a dehydrogenation catalyst containing nickel/chromium, aluminium, copper, manganese and alkali. Compounds of this type which are mentioned in the exemplary embodiments are binuclear aromatic imines.

Dehydrogenation of dicyclohexylamine to give diphenylamine over noble metal catalysts has also already been proposed (German Offenlegungsschrift 3,801,754).

The processes mentioned require starting materials which are relatively expensive to prepare, such as N-cyclohexylidene-aniline or dicyclohexylamine, and need to be improved if they are to be applied to a process to be carried out industrially.

SUMMARY OF THE INVENTION

The invention relates to a process for the preparation of diphenylamine of the formula

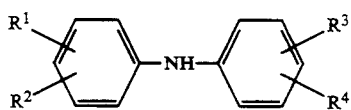

in which $R^1$, $R^2$, $R^3$ and $R^4$, independently of one another, denote hydrogen, $C_1$-$C_4$-alkyl or $C_1$-$C_4$-alkoxy, which is characterised in that anilines of the formula

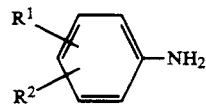

are reacted with cyclohexanones of the formula

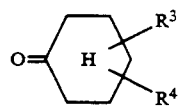

which may be present in a mixture with recycled reaction products, in which in the formulae the radicals $R^1$-$R^4$ have the above meaning, and in which aniline and cyclohexanone are present in a molar ratio of 1:10–10:1, preferably 1:2–6:1, over a supported catalyst containing 0.05–5% by weight, preferably 0.05–4% by weight, particularly preferably 0.1–3% by weight, relative to the total weight of the catalyst, of rhodium or a rhodium/platinum metal combination at 200°–450° C. and 0.1–20 bar.

DETAILED DESCRIPTION OF THE INVENTION

In the process according to the invention, the first step is obviously condensation of aniline with cyclohexanone, which can be assumed to lead, with the elimination of water, to N-cyclohexylidene-aniline, which is then dehydrogenated to diphenylamine. The successful course of the process according to the invention is surprising in various ways. Thus, it is known that the formation of N-cyclohexylidene-aniline is an equilibrium reaction, which always allows significant amounts of the starting materials to be present. Thus there was always the danger that the cyclohexanone would be aromatised to give phenol, which is of no value in this process. Furthermore, it would have been expected that the intermediate formation of N-cyctohexylidene-aniline would not be very favoured, since its formation requires extremely acidic catalysts.

Another surprising fact of the process according to the invention is that not only does the formation of phenol from the cyclohexanone, which is quite conceivable, as described above, not take place but added phenol even reacts in the same manner as cyclohexanone, and consequently, in accordance with the working hypothesis described above, even conversion of phenol into cyclohexanone must take place. The amount of this added phenol, which, in order to avoid unnecessary product mixtures, should have the same substitution pattern as the cyclohexanone used, is 0–20 mol %, relative to the total amount of the mixture of cyclohexanone and phenol.

The catalyst to be used according to the invention contains rhodium or a combination of rhodium with one other platinum metal from the group comprising palladium, platinum, ruthenium and iridium. The noble metals are present in a total amount of 0.05–5% by weight, preferably 0.05–4% by weight, particularly preferably 0.1–3% by weight, relative to the total weight of the catalyst.

Preferably, the catalyst to be used according to the invention contains a combination of rhodium with at least one of the other platinum metals mentioned in which rhodium is present in an amount of 10–90% of the total weight of all noble metals. Particularly preferably, rhodium is combined with palladium or platinum or a mixture of palladium and platinum. Very particularly preferably, palladium by itself or platinum by itself is used for the combination with rhodium. In such a combination, the rhodium content is 10–90%, preferably 15–80%, particularly preferably 20–70%, of the total weight of all noble metals.

The catalyst to be used furthermore contains 1–12% by weight, preferably 2–10% by weight, relative to the weight of the catalyst, of one or more alkali metal hydroxides and/or alkali metal sulphates, the amounts of hydroxides and sulphates being each at most 6% by weight, preferably at most 5% by weight. Examples of such hydroxides and sulphates are: lithium hydroxide, sodium hydroxide, potassium hydroxide, rubidium hydroxide, caesium hydroxide, preferably lithium hydroxide, sodium hydroxide, potassium hydroxide, particularly preferably sodium hydroxide or potassium hydroxide; lithium sulphate, sodium sulphate, potassium sulphate, rubidium sulphate, caesium sulphate, preferably lithium sulphate, sodium sulphate, potassium sulphate, particularly preferably sodium sulphate or potassium sulphate.

The components mentioned of the catalysts to be used are arranged on a support. Examples of such supports are alumina, aluminium spinel, activated carbon, silica gel, bentonite, pumice, zirconium oxide, titanium oxide, zinc oxide, magnesium oxide and rare earth oxides.

The components mentioned of the catalysts to be used are preferably arranged on a support made of altunina or an aluminium spinel, particularly preferably on an alumina or aluminium spinel which has been treated with chromium and manganese. Suitable aluminas are in particular the $\alpha$- and $\gamma$-modification. Aluminium spinels are compounds of the formula

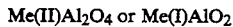

$$Me(II)Al_2O_4 \text{ or } Me(I)AlO_2$$

in which Me(II) is a divalent metal cation of iron, zinc, nickel, copper, cobalt, cadmium, magnesium or other metals, preferably of magnesium, and Me(I) is a monovalent cation, for example lithium (lithium/aluminium spinel). The aluminium in the spinels can be replaced in part by trivalent iron, chromium or manganese. Preferably, $Al_2O_3$, particularly preferably $\gamma$-$Al_2O_3$, is used. Such a support particularly preferably has a combined chromium and manganese content of about 0.05–8% by weight, preferably 0.2–5% by weight, relative to the total weight of the catalyst. The weight ratio of chromium to manganese is 5:1–1:5, preferably 2:1–1:2. Such chromium- and manganese-treated supports are disclosed in EP 208,933.

Preferably, the procedure for preparing the catalysts described is such that chromium and manganese compounds are applied to $Al_2O_3$ in the form of extruded pieces, pills or balls having dimensions of about 2–10 mm, the support thus covered is heated to an elevated temperature, the noble metals and one or more of the alkali metal hydroxides and/or one or more of the alkali metal sulphates are then applied separately; after each application, a drying, in general at 100°–140° C. at reduced to atmospheric pressure, for example 1–1000 mbar, preferably 10–500 mbar, for example under a water pump vacuum, is carried out.

Application of the chromium and manganese to the catalyst support can take place, for example, by joint precipitation of a manganese/chromium hydroxide mixture from a solution of a chromium salt and manganese salt by means of alkali metal hydroxide solution or ammonia, followed by washing off the soluble portions with water. Suitable chromium salts and manganese salts are in particular the sulphates, chlorides, acetates and/or nitrates of the elements mentioned. The deposition of the chromium and manganese on the catalyst support can also take place as ammonium/manganese chromate or ammonium/alkali metal/manganese chromate from a solution of manganese(II) salts and ammonium bichromate by means of ammonia and/or basic alkali metal compounds. Particularly uniform and strongly adhering deposits are obtained by adding the base slowly and uniformly while avoiding excessively large differences in concentration.

To this end the precipitation can, for example, be carried out by means of urea under hydrolysing conditions, which particularly efficiently ensures that the conditions of slow base addition are fulfilled.

After application of the chromium compounds and manganese compounds and the precipitation described, the catalyst support thus coated is washed until free of soluble compounds, before being heated to elevated temperatures (about 200°–450° C., preferably 250°–350° C.). After this heat treatment, the chromium- and manganese-coated support is ready for impregnation with the remaining catalyst components mentioned.

Impregnation of the catalyst with the noble metals or with alkali metal hydroxide and/or alkali metal sulphate (one or more of each of these) is carried out separately.

The procedure can be such that the support is first impregnated with the noble metals, for example in the form of aqueous solutions of their chlorides, nitrates, acetates or other suitable salts, a further impregnation with a solution of alkali metal hydroxide and/or alkali metal sulphate being carried out after the drying. This treatment precipitates the noble metals in the form of their oxides or hydroxides. Impregnation of the support with the alkali metal hydroxide(s) and the alkali metal sulphate(s) can take place separately or jointly. After a final drying, the catalyst is available for use.

Before being used, it is preferably activated by a treatment with hydrogen at elevated temperature, for example at 120°–400° C., preferably at 150°–380° C. This activation can particularly advantageously take place in the reactor in which the preparation according to the invention of diphenylamine is then carried out.

However, it is also possible to impregnate the support first with an alkali metal hydroxide solution, followed by drying, and to apply the noble metal salts mentioned to the thus pretreated, basified catalyst support, impregnation taking place simultaneously with precipitation of the noble metals in the form of their oxides or hydroxides. In this variant, the additional impregnation with alkali metal sulphates can take place together with the alkali metal hydroxide, before or after application of the alkali metal hydroxide, or as final impregnation after application of the noble metals. In this case too, each impregnation is followed by a separate drying step. After subsequent drying, the catalyst is, in this case too, again ready for use but can first also be activated in the manner described, using hydrogen at elevated temperature.

Instead of impregnating the support mentioned, in order to coat it with the substances mentioned, it is also possible to spray it with suitable solutions. The apparatuses necessary for all these operations and the production of the desired coating rate by selection of the amount and concentration of the solutions of the elements mentioned are known in principle to one skilled in the art.

Apart from aqueous solutions, alcoholic solutions or solutions in lower carboxylic acids or lower amines are in principle also suitable, as long as the intended noble metal salts or the basic alkali metal compounds or the sulphates are soluble therein.

Examples of $C_1$–$C_4$-alkyl or $C_1$–$C_4$-alkoxyin the substituents $R^1$–$R^4$ are methyl, ethyl, propyl, isopropyl, butyl, isobutyl, methoxy, ethoxy, propoxy, isopropoxy, butoxy or isobutoxy. Preferably, the substituents mentioned have 1–2 C atoms, particularly preferably they are methyl or methoxy. Furthermore, the substituent $R^2$ or $R^4$ is preferably hydrogen, while the substituents $R^1$ and $R^3$ adopt the scope of meaning mentioned. Particularly preferably, the process is directed to the preparation of unsubstituted diphenylamine.

The starting compounds aniline and cyclohexanone or aniline and cyclohexanone/phenol mixture are used in a molar ratio of 1:10–10:1, preferably 1:2–6:1. The starting compounds are evaporated individually or jointly, and the resulting vapour mixture is transported to the rhodium-containing catalyst described above, if necessary by means of a carrier gas stream. Examples of carrier gases for this purpose are nitrogen, hydrogen, argon, lower hydrocarbons, such as methane, ethane or natural gas and mixtures thereof. Preferably, nitrogen or hydrogen or a mixture thereof is used as the carrier gas. The carrier gas is used in an amount of 1–100 l/g of starting material, preferably 1–50 l/g of starting material. The space velocity is set to 0.01–1 kg of starting material per 1 of catalyst and hour.

Apart from the starting compounds mentioned, aniline and cyclohexanone, and the partial replacement already described of cyclohexanone by the corresponding phenol, further substances, such as N-cyclohexylidene-aniline or dicyclohexylamine or N-cyclohexyl-aniline, can be used.

The process according to the invention is carried out at a temperature of 200°–450° C., preferably 250°–420° C., and a pressure of 0.1–20 bar, preferably 1–6 bar, in the gas phase. The combination of reaction temperature and reaction pressure are selected in a manner known to one skilled in the art in such a manner that the reaction can always be carried out in the gas phase.

EXAMPLE 1

40 ml (37 g) of rhodium catalyst, prepared according to EP 208,933, Example 5, was placed in a electrically heated tube of 80 cm in length and 17 mm in diameter. The catalyst was first activated in a hydrogen stream (15–20 l/h) at 400° C. for 69 hours. At a catalyst temperature of 290° C., an aniline/cyclohexanone mixture in a molar ratio of 4:1 was passed over the catalyst using a suitable metering device. 13 l/h of nitrogen were used as the carrier gas. In the upper portion of the reaction tube, in which only packing material was present, the mixture of the starting materials evaporated and passed, together with the carrier gas, through the catalyst bed, which was present in the middle portion of the reaction tube. The reaction product formed was condensed and analysed by gas chromatography. Under stationary reaction conditions at a space velocity of 0.36 g of mixture of starting materials/ml of catalyst×h, the following reaction product was obtained:

| Diphenylamine | 36.4% |

-continued

| N-Cyclohexyl-aniline | 0.15% |
| Phenol | 0.4% |
| Aniline | 62.9% |
| By-products | Balance |

EXAMPLE 2

A reaction tube having a diameter of 17 mm and a length of about 600 mm and whose upper portion served as evaporation zone and whose lower portion was filled with 30 ml of an Rh/Pd catalyst prepared according to German Offenlegungsschrift 3,801,754, Example 2, was maintained at 400° C. by electrical heating. At this temperature, the catalyst was first activated in an $H_2$ stream for 65 hours. 188 g of a mixture of 4 mol of aniline and 1 mol of cyclohexanone and 10 l of $N_2$/h were passed into the reaction tube over a period of 25 hours, using a calibrated metering device. The reaction product was condensed and analysed by gas chromatography. The following composition was found:

| Diphenylamine | 48.6% |
| N-Cyclohexyl-aniline | 1.8% |
| N-Cyclohexylidene-aniline | 0.4% |
| Aniline | 47.2% |
| Phenol | 0.4% |
| By-products | Balance |

EXAMPLE 3

A reaction tube having a diameter of 32 mm and a length of 80 cm was used for reacting aniline and cyclohexanone to give diphenylamine. 200 ml (175.4 g) of catalyst were used which had been prepared according to German Offenlegungsschrift 3,801,754, Example 2, from spherical (2–6 mm) γ-$Al_2O_3$ by impregnating this support with 1% of Cr, 1.1% of Mn, 0.5% of Rh, 0.5% of Pt, 2.7% of NaOH and 2.7% of $K_2SO_4$.

The catalyst was first activated at 400° C. in a hydrogen stream (60 l/h) for 72 hours. A mixture of aniline and cyclohexanone was then passed over the catalyst together with nitrogen as the carrier gas (12 to 40 l/h) at 315° to 335° C. The reaction product was condensed and analysed by gas chromatography. The following composition was found as a function of the hours on stream of the catalyst at various reaction conditions (balance to 100% are by-products):

| Hours on stream of the catalyst (h) | Aniline: cyclohexanone (mol/mol) | Space velocity (g/ml × h) | Temperature (°C.) | Diphenylamine % by area* | Aniline % by area* | Phenol % by area* |
| --- | --- | --- | --- | --- | --- | --- |
| 100 | 5 | 0.3 | 335 | 29.7 | 69.6 | 0.3 |
| 194 | 5 | 0.3 | 332 | 32.2 | 67.7 | — |
| 240 | 4 | 0.4 | 330 | 33.7 | 65.7 | 0.5 |
| 266 | 4 | 0.4 | 331 | 36.1 | 63.4 | 0.5 |
| 334 | 4 | 0.5 | 330 | 37.2 | 62.2 | 0.6 |
| 454 | 4 | 0.4 | 330 | 39.1 | 60.3 | 0.6 |
| 595 | 4 | 0.4 | 322 | 40.2 | 58.7 | 0.6 |
| 737 | 4 | 0.4 | 322 | 37.9 | 61.5 | 0.6 |
| 783 | 4 | 0.4 | 323 | 37.4 | 61.5 | 0.6 |
| 876 | 4 | 0.4 | 315 | 36.2 | 62.6 | 0.7 |

*% by area = per cent by area of gas chromatographic analysis

What is claimed is:

1. A process for the preparation of a diphenylamine of the formula

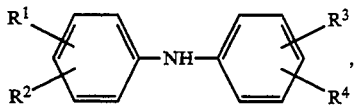

in which

R¹, R², R³ and R⁴ independently of one another denote hydrogen, $C_1$-$C_4$-alkyl or $C_1$-$C_4$-alkoxy, wherein an aniline of the formula

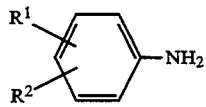

is reacted in the gas phase with a cyclohexanone of the formula

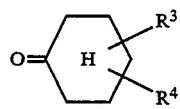

in which in the formulae the radicals R¹–R⁴ have the above meaning, and in which aniline and cyclohexanone are present in a molar ratio of 1:10–10:1 over a supported catalyst containing 0.05–5% by weight of rhodium or a rhodium/platinum metal combination at 200°–450° C. and 0.1–20 bar.

2. The process of claim 1, wherein the molar ratio of aniline and cyclohexanone is 1:2–6:1.

3. The process of claim 1, wherein the reaction is carried out at 250°–420° C.

4. The process of claim 1, wherein the reaction is carried out at 0.1–6 bar.

5. The process of claim 1, wherein the catalyst contains a rhodium/platinum metal combination in which rhodium represents 10–90% by weight of all noble metals and the platinum metals are those from the group consisting of palladium, platinum, ruthenium and iridium.

6. The process of claim 5, wherein rhodium represents 15–80% by weight of all noble metals in the catalyst.

7. The process of claim 6, wherein rhodium represents 20–70% by weight of all noble metals in the catalyst.

8. The process of claim 1, wherein the support is alumina.

9. The process of claim 8, wherein the support is an alumina treated with chromium and manganese.

10. The process of claim 1, wherein the catalyst additionally contains 1–12% by weight, relative to the total weight of the catalyst, of one or more alkali metal hydroxides and/or alkali metal sulphates, the amounts of hydroxides and sulphates being each at most 6% by weight.

11. The process of claim 1, wherein 0–20 mol % of the cyclohexanone is replaced by the corresponding phenol.

* * * * *

UNITED STATES PATENT AND TRADEMARK OFFICE
CERTIFICATE OF CORRECTION

PATENT NO. : 5,338,885
DATED : August 16, 1994
INVENTOR(S) : Otto IMMEL, et al.

It is certified that error appears in the above-identified patent and that said Letters Patent is hereby corrected as shown below:

| | |
|---|---|
| Column 7, line 30, | before "catalyst" cancel "supported" |
| Column 7, lines 31 and 32, | after "combination" insert --supported on an alumina treated with chromium and manganese-- |
| Column 7, line 32, | after "at" insert --a temperature of-- |
| Column 7, line 32, | after "and" insert --a pressure of-- |
| Column 8, lines 19 to 22, | cancel "claims 8 and 9" |

Signed and Sealed this

Fifteenth Day of June, 1999

Attest:

Q. TODD DICKINSON

*Attesting Officer*   Acting Commissioner of Patents and Trademarks